United States Patent [19]

Terada et al.

[11] 4,400,534
[45] Aug. 23, 1983

[54] ANALGESIC AND ANTI-INFLAMMATORY AGENTS

[75] Inventors: Atsusuke Terada; Eiichi Misaka, both of Hiromachi, Japan

[73] Assignee: Sankyo Company, Limited, Tokyo, Japan

[21] Appl. No.: 331,616

[22] Filed: Dec. 17, 1981

[30] Foreign Application Priority Data

Dec. 23, 1980 [JP] Japan .............................. 55-182684

[51] Int. Cl.³ ............................................. C07C 59/00
[52] U.S. Cl. .................................... 562/468; 560/57; 560/51; 562/459; 564/181; 424/317
[58] Field of Search ......................... 560/57; 562/468; 424/317

[56] References Cited

U.S. PATENT DOCUMENTS 3,649,678  3/1972  Fusco et al. ........................ 562/468
4,137,324  1/1979  Elliott et al. ......................... 560/51

Primary Examiner—Paul J. Killos
Attorney, Agent, or Firm—Frishauf, Holtz, Goodman & Woodward

[57] ABSTRACT

Compounds of formula (I):

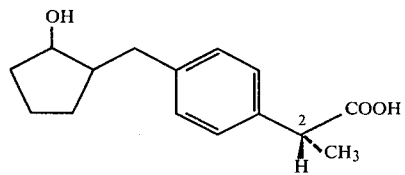

(I)

its salts, and resolved forms thereof, especially the compound of formula (II):

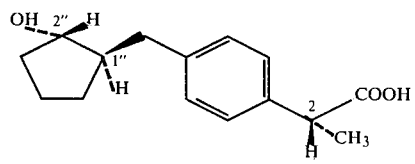

(II)

and its salts are new analgesic and/or anti-inflammatory agents. The agents are prepared by resolution at the 2-position of a suitable starting material such as the compound (IV):

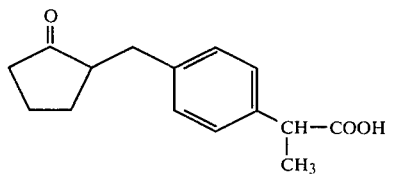

(IV)

or an optionally partly resolved form thereof, with subsequent reduction and optional resolution to give the trans form.

5 Claims, No Drawings

ANALGESIC AND ANTI-INFLAMMATORY AGENTS

This invention relates to analgesic and anti-inflammatory agents. It further relates to pharmaceutical compositions containing the new agents, and to processes for preparing the new agents.

In U.S. Pat. No. 4,161,538 there are described anti-inflammatory agents which include various 4-(2-oxocycloalkylmethyl)phenylacetic acid derivatives. Related 4-(2-oxocycloalkylidinemethyl)phanylacetic acid derivatives are disclosed in U.S. Pat. No. 4,254,274. Furthermore, in Japanese laid-open application No. 127041/76, there is a general disclosure of 2-(substituted-phenyl)alkanoic acid derivatives for use as anti-inflammatory and analgesic agents.

As a result of extensive studies into non-steroidal anti-inflammatory and analgesic agents, we have unexpectedly discovered that high activity resides in a particular form of a particular 4-(2-hydroxycyclopentylmethyl)phenylpropionic acid compound.

In accordance with the present invention we provide (2S)-2-[4-(2-hydroxycyclopentan-1-ylmethyl)phenyl]-propionic acid and its pharmaceutically acceptable salts. The acid is of the formula (I):

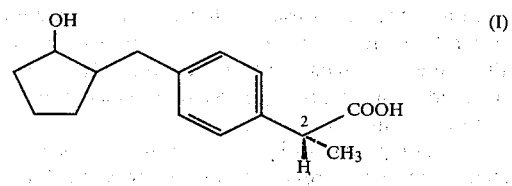

The acid (I) is of (S) configuration at the 2-position, but has two other asymmetric carbon atoms and exists as isomers which form part of this invention.

Thus, as a preferred aspect of this invention, we provide the (1″R,2″S) isomer of the compound of formula (I) and its pharmaceutically acceptable salts. This isomer is (2S)-2-{4-[(2S,1R)-2-hydroxycyclopentan-1-ylmethyl]phenyl}-propionic acid of formula (II):

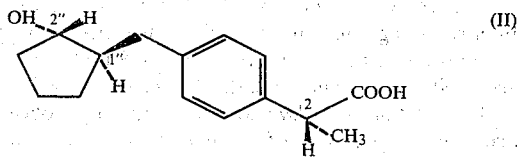

In this compound (II) the (1″R) and (2″S) substituents are in a trans relationship, and we also refer to this compound as a trans isomer of the compound (I). There is another trans isomer of the compound (I), namely the (2S,1″S,2″R) isomer of the formula (III):

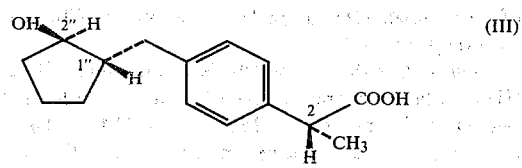

Mixtures of compounds (II) and (III) are herein also referred to as the trans form of compound (I) and are part of this invention. In a like manner, the (1″S,2″S) and (1″R,2″R) isomers of compound (I) constitute the cis form and are also part of this invention. The compounds of this invention show potent inhibition of prostaglandin-biosynthesis enzyme activity, with the compound (II) and its salts being more active than the compound (I) and its salts.

In accordance with this invention, there is also provided a process for preparation of the active compounds. For convenience, in the following definition and discussion of the process, we use the abbreviation "The Acid" for 2-[4-(2-hydroxycyclopentan-1-ylmethyl)phenyl]propionic acid". Thus, for example, a reference to "a (2″S) isomer of The Acid" is a reference to any isomer of 2-[4-(2-hydroxycyclopentan-1-ylmethyl)]propionic acid which has S chirality at the 2″-position.

The process of the present invention comprises resolution of a (2S) isomer of The Acid or a precursor for The Acid from a mixture of (2S) and (2R) isomers, and where necessary conversion of the resolved precursor to the corresponding (2S) isomer of The Acid; and optional salification to give a pharmaceutically acceptable salt.

Where resolution is performed on racemic starting material, the product is the compound of formula (I) with unresolved stereochemistry at the 1″- and 2″-positions. If desired, the trans form of compound (I) can then be separated out, giving the compound (II) in admixture with compound (III).

As one alternative, the resolution can be performed on partially resolved starting material, for instance a mixture of (2S,1″R) and (2R,1″S) isomers. This product can then be resolved to give the compound (II), the (2S,1″R,2″S) isomer.

In practice, the mixture of isomers which is resolved will usually be a 50:50 mixture such as occurs naturally. Resolution can be effected in a conventional manner, for example by preferential crystallization, by high-pressure liquid chromatography or by formation of a diastereoisomeric derivative. Such techniques are also applicable to the optional resolutions and separations indicated above.

The resolution can be effected on The Acid itself or on a precursor for The Acid. The precursor can be any compound which by reaction can be converted to The Acid with retention of the resolved optical activity. By way of example, the precursor can be the known compound, 2-[4-(2-oxocyclopentan-1-ylmethyl)phenyl]propionic acid. Reduction of this compound after resolution effects a simple conversion to the desired (2S) isomer of The Acid. More generally, the preparative procedures described in the patent literature mentioned above can be tailored to suit the purposes of the present invention.

Illustrative methods embodying the process of this invention will now be described with reference to the following reaction schemes entitled Method A and Method B.

METHOD A

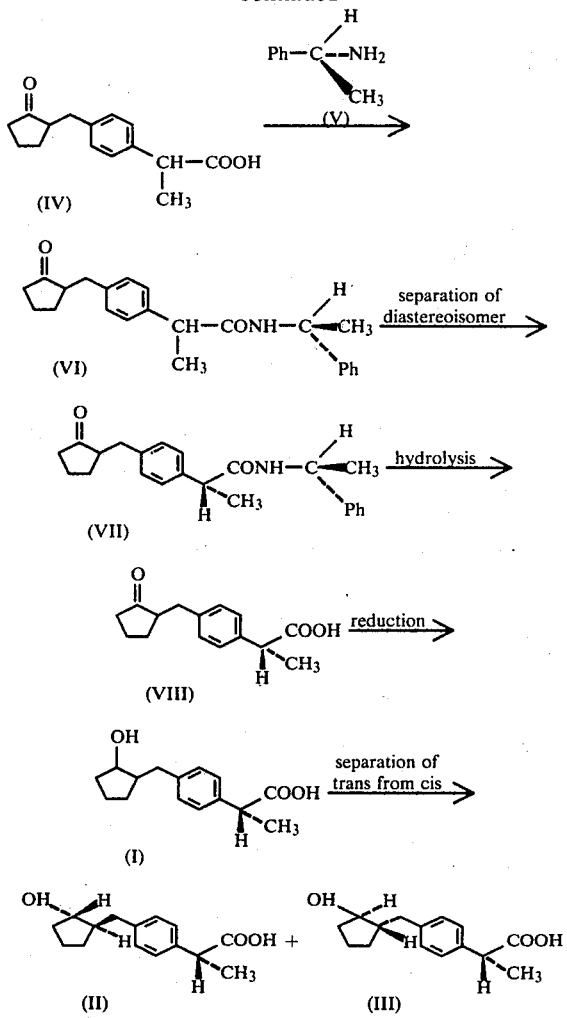
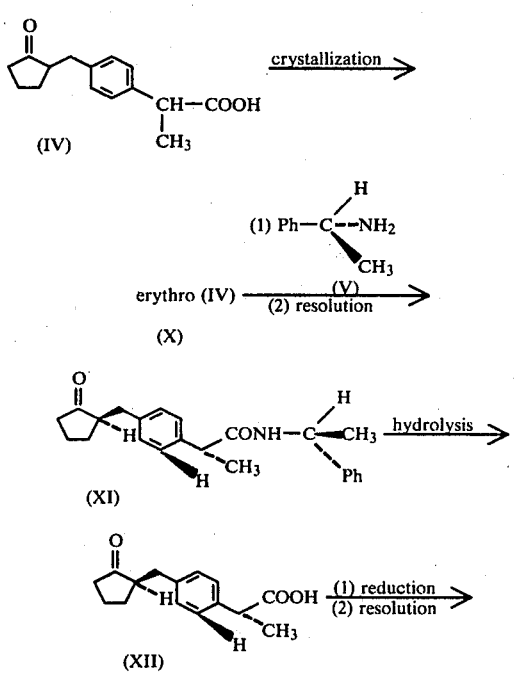

METHOD B

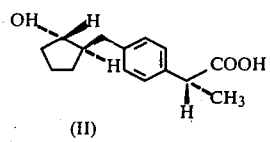
(II)

In the Method A, the compound of formula (I) is prepared by resolution of the known keto compound (IV) using diastereoisomer formation, giving the (2S)-precursor (VIII) which is then converted by reduction to the desired (2S) isomer of The Acid; (2S)-2-[4-(2-hydroxycyclopentan-1-ylmethyl)phenyl]propionic acid.

Considering in more detail the illustrative sequence shown in the reaction scheme for Method A, the compound (VI) can be obtained by condensing the racemic keto compound of formula (IV) with the amine compound (V) which is an optically active (S) isomer. The condensation can be effected directly, using a condensing agent such as dicyclocarbodiimide (DCC), or pyridinedisulphide-triphenylphosphine or 2-fluoro-1-methylpyridinium paratoluenesulphonate in the presence of an inert organic solvent (for example, a halogenated hydrocarbon such as dichloromethane, an ether such as tetrahydrofuran or dioxane or an aromatic hydrocarbon such as benzene or toluene.) Alternatively, the condensation can be effected indirectly, for example by condensing an alkyl carbonate of the compound (IV) with the compound (V).

The compound (VI) is then resolved using for instance high-pressure liquid chromatography ("hplc") to separate the compound (VII) of (S,S)-configuration. This particular diastereoisomer is then hydrolyzed with nitrogen peroxide or other hydrolyzing agent to obtain the compound (VIII) which is the (2S)-isomer of the starting keto compound of formula (IV).

It will be appreciated that the use of the amine of formula (V) is not essential, and that other means can be obtained to resolve the (2S)-isomer of formula (VIII) from the racemic starting material of formula (IV).

The resolved compound (VIII) can then be reduced by a reducing agent which will reduce the keto group without reducing the carboxyl group. Suitable reagents are well known and include, for example, a hydride such as sodium borohydride or sodium cyanoborohydride in the presence of an inert organic solvent (for example, an ether such as tetrahydrofuran or ethyl ether, an aromatic hydrocarbon such as benzene or toluene, or the like solvent). The reduction gives the desired compound of formula (I).

As shown in the reaction scheme of Method A, the trans form of The Acid can then be obtained by resolution of the compound of formula (I). Thus, the mixture of compounds (II) and (III) can be obtained by hplc of the compound (I).

As shown in the Method B, the compound of formula (II) is obtained by resolution of a partly resolved starting material, a mixture of (2S,1"R) and (2R,1"S) isomers known as the erythro form. In this instance the erythro form (X) of precursor keto compound (IV) is employed, giving the (2S,1"R)-precursor (XI) which is hydrolyzed and then reduced to a mixture of (2S,1"R,2"R) and (2S,1"R,2"S) which is then resolved to give the desired (2S,1"R,2"S) isomer of The Acid, (2S)-2-{4-[(1R,2S)-2- hydroxycyclopentan-1-ylmethyl]phenyl}propionic acid.

Considering in more detail the illustrative sequence shown in the reaction scheme for Method B, the erythro form of compound (IV), that is the compound (X), can be obtained by repeated recrystallization of the compound (IV) from a suitable organic solvent (for example, an ester such as ethyl acetate, an aromatic hydrocarbon such as benzene or toluene, an ether such as ethyl ether or tetrahydrofuran, an alcohol such as methanol or ethanol, or a mixture of one or more of these solvents and one or more aliphatic hydrocarbons such as hexane, ligroin petroleum ether). The compound (X) is then reacted with the optically active compound (V) in a similar manner to that discussed for Method A. Resolution of the amido compound by hplc or other procedure then gives the d-erythro form, compound (XI). The compound (XI) can then be hydrolized to obtain the resolved keto compound of formula (XII). Hydrolysis can be effected in the same manner as for Method A.

The compound (XII) can then be reduced as in the Method A, giving a mixture which can be separated into the cis and trans compounds, for example by use of hplc, thereby giving the desired compound (II) of (2S,1″R,2″S) configuration.

Reflecting the preferred procedures contained within the Methods A and B, the present invention further provides a process for the preparation of the present compounds which process comprises optional resolution of the compound (IV) to give the erythro form, resolution at the 2-position of the optionally resolved compound (IV) to give the isomer of the compound (IV) or of the erythro form, said isomer having (2S) stereochemistry, reduction to give the corresponding (2S) isomer of The Acid, and optional resolution to give the compound (II) alone or in admixture with the other trans isomer, as the case may be. The optional final step gives the compound (II) in admixture with the other isomer when the first optional resolution is omitted.

By whatever process the present compounds are prepared, they can if desired be converted to a pharmaceutically acceptable salt. Examples of suitable salts include an alkali metal or alkaline earth metal salts, such as a sodium or calcium salt; an aluminum salt; an ammonium salt; a salt with an organic base such as triethylamine, dicyclohexylamine, dibenzylamine, morpholine, piperidine or N-ethylpiperidine; or a salt with a basic amino acid such as lysine or arginine.

The following examples 1 and 2 are illustrative of the preparation of the present novel compounds using methods in accordance with our invention.

EXAMPLE 1

(2S)-2-[4-(2-Hydroxycyclopentan-1-ylmethyl)phenyl]-propionic acid (compound (I)) and its trans form.

1.2 g of 2-[4-(2-oxocyclopentan-1-ylmethyl)phenyl]-propionic acid, 1.1 g of pyridinedisulphide and 1.31 g of triphenylphosphine were dissolved in 10 ml of methylene chloride. The resulting solution was stirred with ice-cooling for 10 minutes. 0.6 g of l-α-phenylethylamine (that is, the notional S-isomer) was added to the solution which was then stirred at room temperature for 30 minutes. Methylene chloride was distilled off, and the residue chromatographed using high-pressure liquid chromatography to give 3.0 g of the compound (VII), the (S)-α-phenylethylamide of the starting acid, otherwise referred to as the l-α-phenylethylamide of the starting acid.

28 g of sodium acetate was suspended in 160 ml of carbon tetrachloride. The resulting suspension was cooled to −78° C. and 25 ml of carbon tetrachloride solution containing 1.5 moles of nitrogen peroxide was added. The mixture was then stirred for 10 minutes at 0° C., 3.0 g of the compound (VII) as prepared above was added to the mixture, and the resultant system was stirred for 2 hours at 0° C. 160 ml of water was then added and the carbon tetrachloride layer separated, washed with water and refluxed for 40 minutes. The carbon tetrachloride was thereafter distilled off and the residue purified by column chromatography on silica gel to afford 800 mg of crystals. The crystals were recrystallized from ether-hexane to give 720 mg of crystals of compound (VIII), (2S)-2-[4-(2-oxocyclopentan-1-ylmethyl)-phenyl]propionic acid, melting at 57° to 59° C. The resolved compound (VIII) was dissolved in 15 ml of tetrahydrofuran and 400 mg of sodium cyanoborohydride was then added. The mixture was maintained at pH 3 with 3 N-methanol/hydrochloric acid while ice-cooling, and was then stirred for 40 minutes. Ice-water was then added, and the mixture extracted with ether. The ether extract was dried over sodium sulphate and the solvent distilled off to give 680 mg of compound (I), with unresolved 1″- and 2″-positions. By our alternative terminology, this mixture is a mixture of the cis and trans compounds.

The product was recrystallized from ethyl acetate-hexane to afford crystals of compound (I) melting at 126° to 130° C. The crystals did not always show a constant melting point when melted with various mixtures in which the ratio of the cis compound and the trans compound was varied.

The crystalline product was then subjected to high-pressure liquid chromatography to obtain the trans compound [the (2S,1″R,2″S) and (2S,1″S,2″R) isomers, respectively compound (II) and compound (III)]. It was then recrystallized from ether-hexane to afford crystals melting at 87° to 95° C.

Elementary analysis—Calcd for $C_{15}H_{20}O_3$: C, 72.55; H, 8.12; Found: C, 72.39; H, 8.11.

EXAMPLE 2

(2S)-2-{4-[(1R,2S)-2-Hydroxycyclopentan-1-ylmethyl]-phenyl}propionic acid (compound III))

1-[4-(2-oxocyclopentan-1-ylmethyl)phenyl]propionic acid was recrystallized several times from ethyl acetate-hexane to obtain a (2S,1″R),(2R,1″S) mixture, compound (X), melting at 108.5° to 111° C. By analogy, we also call this compound (X) the erythro form of compound (IV).

The l-α-phenylethyl amide derivative of the compound (X) was then prepared using the same procedures as in Example 1, and subjected to optical resolution using high-pressure liquid chromatography to give the l-amide of the (2S,1″R) compound, namely compound (XI). This product was then treated with nitrogen peroxide in the same manner as in Example 1 and the resultant acid recrystallized from ether-hexane to afford the (2S,1″R) isomer, compound (XII), melting at 61° to 62° C.

123 mg of the compound (XII) and 75 mg of sodium cyanoborohydride were dissolved in 5 ml of methanol. The resulting solution was adjusted to pH 3 with 6 N-hydrochloric acid while ice-cooling. After the solution had been stirred for 40 minutes, ice-water was added and the resultant system extracted with ether. The ether extract was washed with water, dried, and the solvent distilled off to obtain crystals which were subjected to high-pressure liquid chromatography. This separation of the isomers gave the desired (2S,1"R,2"S) compound of formula (II). The product was recrystallized from ethyl acetate-hexane to afford 40 mg of crystals of compound (II) melting at 87° to 88° C.

Elementary analysis—Calcd for $C_{15}H_{20}O_3$: C, 72.55; H, 8.12 Found: C, 72.41; H, 8.24.

The potent activity of the compounds of this invention is illustrated by the following report of pharmacological testing.

Pharmacological Testing

The inhibitory activities of the present compounds in prostaglandinbiosynthesis were tested in comparison with indomethacin in order to assess activity as an analgesic and/or anti-inflammatory agent.

Microsome tests were conducted according to the methods of E Takeguchi, E Kohno, C J Sih: Biochemistry 10, 2372 (1971), "Preparation of bovine seminal vesicle" and of R J Flower, H S Cheung, D W Cushman: Prostaglandins 4, 325 (1973), "Pharmacological action system."

The compounds under test were added to a system comprising microsome prostaglandin-biosynthesis enzyme (1mg/ml) fractionated from bovine seminal vesicles, glutathione (2 mM), epinephrine (1 mM) and trisaminomethane-hydrochloric acid buffer solution pH 7.6 (0.1 M). The mixture was left to stand at 30° C. for 5 minutes and commercially available $^{14}C$-arachidonic acid (10 μM, 50–60 nCi) was added. The resultant solution was maintained at 30° C. for 10 minutes and reaction then stopped by addition of 0.1 N hydrochloric acid. After extraction of the reaction mixture, the extract was separated by thin layer chromatography on silica gel to give the prostaglandin which was produced. The main product, prostaglandin $E_2$, was measured using a liquid scintillation counter in accordance with the method of L Levine et al: Journal of Biological Chemistry (246, 6782 (1971). The inhibitory activities were assayed by the radioactivity ratio of the sample to a blank.

The results are given in the following table 1.

The inhibition of prostaglandin-biosynthesis by the compounds under test was assayed by an in vivo method using cultured cells, as described by P J Carty et al Prostaglandins 19, 51 (1980). 3T6 cells from mouse fibroblasts were used as the cultured cells.

About six hundred thousand 3T6 cells were cultured in a plastics Petri dish (35 mm inner diameter) at 37° C. for 48 hours using a minimum-requirement medium, Darbecco (Trade Mark). After culturing, the cells were separated, washed, and then contacted with the same medium but containing the compound under test. After contacting for 2 hours, the medium was separated off and the cells washed. The medium containing 5 μg/ml of arachidonic acid and the test compound were added. Culturing was allowed to continue for 1 hour, and then the concentration of the prostaglandin $E_2$ in the medium was assayed by radioimmunoassay.

The results are also given in the table 1.

TABLE 1

| | Inhibition of PG-biosynthesis enzyme activity | |
|---|---|---|
| Compound | Bovine seminal vesicle microsome $I_{50}$ (μM) | Culture cells $I_{50}$ (μM) |
| I | 72 | — |
| II + III | 13 | — |
| II | 9 | 0.25 |
| IM | 0.4 | 0.34 |

Compounds (I), (II) and (III) are as defined above, while the compound IM is indomethacin. The mix of (II) and (III) was 50:50.

As is apparent from the above results of the pharmacological tests, the compound of formula (I), especially its isomer which is the compound of formula (II), and their pharmacologically acceptable salts show strong promise as analgesic and/or anti-inflammatory agents. The results of the in vivo test are particularly significant, indicating better activity in the compound (II) compared to indomethacin.

Reflecting the potency of the present compound, the present invention further provides a pharmaceutical composition which comprises one or more of the present compounds, together with a pharmaceutical vehicle which may comprise a diluent, binding agent, disintegrant, lubricant and/or taste modifier.

The present compositions can be formulated for administration in various ways. Thus, for example, the compounds can be administered orally in the form of tablets, capsules, granules, powders or syrups, or they can be administered rectally in the form of suppositories. One of the further possible modes of administration is topical application, and to this end the pharmaceutical vehicle will comprise a topical base.

The dosage of the compound will depend upon the condition, age and weight of the patient, among other factors, but will usually be from about 30 to about 300 mg per day per adult taken in single or divided doses.

The following Example 3 is illustrative of the formulations in accordance with the present invention.

EXAMPLE 3

Capsules for oral administration

| Ingredient | Parts by weight |
|---|---|
| (2S)-2-4-[(1R,2S)-2-hydroxycyclopentan-1-ylmethyl)phenyl]propionic acid, compound (II) | 25 |
| lactose | 173.5 |
| corn starch | 100 |
| magnesium stearate | 1.5 |
| total | 300 |

The materials in the prescribed ratios were blended as powders and passed through a screen of 20 mesh. 300 mg of the blended powder was used for each No 3 gelatin capsule.

We claim:

1. (2S)-2-[4-(2-hydroxycyclopentan-1-ylmethyl)-phenyl]propionic acid of the formula (I):

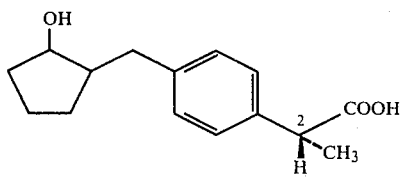
(I)

or a pharmaceutically active salt thereof.

2. The acid of claim 1 or a salt thereof, wherein the 1″ and 2″-substituents are in trans relationship.

3. (2S)-2-{4-[(2S,1R)-2-hydroxycyclopentan-1-ylmethyl[phenyl}propionic acid of the formula (II):

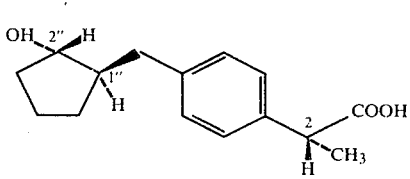
(II)

or a pharmaceutically active salt thereof.

4. A pharmaceutical composition comprising an acid or salt according to any of claims 1, 2 and 3, together with a pharmaceutically acceptable vehicle.

5. A pharmaceutical composition formulated for oral, rectal or topical administration and comprising the acid or salt thereof of claim 3.

* * * * *